United States Patent [19]
Dahms

[11] Patent Number: 5,279,766

[45] Date of Patent: Jan. 18, 1994

[54] POLYESTER SURFACTANT COMPOSITION EMPLOYING POLYOXYALKYLATED ALKYLENE DIAMINE

[75] Inventor: Gerd Dahms, Veltbert, Fed. Rep. of Germany

[73] Assignee: ICI Americas Inc., Wilmington, Del.

[21] Appl. No.: 914,211

[22] Filed: Jul. 14, 1992

Related U.S. Application Data

[63] Continuation of Ser. No. 298,084, Jan. 7, 1989, abandoned.

[30] Foreign Application Priority Data

Jan. 21, 1988 [GB] United Kingdom ............... 8801305

[51] Int. Cl.⁵ .............................................. B01F 17/16
[52] U.S. Cl. ................................... 252/356; 252/357; 106/504; 106/505
[58] Field of Search ................... 252/312, 356, 357; 106/504, 505; 528/291, 288, 300

[56] References Cited

U.S. PATENT DOCUMENTS

| | | |
|---|---|---|
| 3,223,659 | 12/1965 | Curtice et al. .................. 528/297 |
| 3,755,497 | 8/1973 | Weedon et al. ............... 528/291 X |
| 3,787,523 | 1/1974 | Crescentini et al. ........... 525/430 |
| 4,026,941 | 5/1977 | Login et al. .................. 528/291 X |
| 4,029,694 | 6/1977 | Weipert et al. ............... 528/288 X |
| 4,094,796 | 6/1978 | Schwarz .......................... 252/8.8 |
| 4,233,196 | 11/1980 | Sublett ......................... 528/300 X |
| 4,301,048 | 11/1981 | Hirayama et al. .............. 106/252 |
| 4,509,950 | 4/1985 | Baker ............................ 252/356 X |
| 4,521,586 | 6/1985 | Fujita et al. ................... 524/596 |
| 4,909,852 | 3/1990 | Atkinson ...................... 252/357 X |

OTHER PUBLICATIONS

Schwartz, A. M., Surface Active Agents and Detergents, vol. II, Interscience Publ., Inc., (N.Y., 1958) pp. 268-271.

Primary Examiner—Richard D. Lovering
Assistant Examiner—Daniel S. Metzmaier
Attorney, Agent, or Firm—Paul L. Sharer

[57] ABSTRACT

A composition is the reaction product of
(1) a alkylene diamine condensate compound containing a poly(oxyalkylene)group and having at least two —OH groups;
(2) a compound other than as defined in (1) which contains at least two reactive hydrogen atoms present as —OH, —NH₂ or —NHR;
(3) a carboxylic acid containing at least two carboxylic acid groups or an anhydride or chloride thereof; and
(4) a mono-carboxylic acid, a mono-hydroxycompound, a secondary mono-amine or a hindered primary mono-amine;

where components (2) and (3) may be replaced, at least partially, by a substituted carboxylic acid. The resulting composition is non-ionic and can be used to prepare a wide range of emulsions or dispersions of solids in liquids.

16 Claims, No Drawings

POLYESTER SURFACTANT COMPOSITION EMPLOYING POLYOXYALKYLATED ALKYLENE DIAMINE

This is a Continuation of copending application Ser. No. 07/298,084 filed on Jan. 17, 1989 and now abandoned.

The present invention relates to compositions which have surfactant properties and to emulsions and dispersions which contain such compositions.

A wide range of materials are known which have surfactant properties and many such materials are commercially available. Some of these are relatively simple materials such as esters of polyols with long chain carboxylic acids, for example sorbitan monostearate. Other more complex materials contain a polymeric group and may include an anionic or cationic grouping or may be non ionic.

One type of surfactant which is commercially available is based on polyoxyalkylenes, particularly polyoxyethylene, and includes condensates of polyoxyalkylenes with phenols, especially those having at least one higher alkyl substituent, or fatty alcohols, condensates of polyoxyalkylenes with amines, especially polyamines such as ethylene diamine and also block copolymers containing polyoxyethylene and polyoxypropylene sequences. The terms "fatty" and "higher alkyl" are used herein in respect of alkyl groups having at least six carbon atoms, particularly at least eight carbon atoms and especially at least twelve carbon atoms and includes straight and branched chain alkyl groups and mixtures thereof.

A further type of surfactant is based on polyesters, for example the self-condensation products of hydroxycarboxylic acids, which may contain end groups derived from a primary, secondary or tertiary amino group or a salt thereof with an acid or a quaternary ammonium salt group as described in GB 1373660 or end groups derived from a polyalkylene glycol or a polyether polyol as described in GB 2002400.

Yet a further type of surfactant is based on a long chain mono- or poly-carboxylic acid or anhydride, for example a polyalk(en)yl succinic anhydride. These materials may be modified by reaction of the acid or anhydride group with a compound which is at least bi-functional such as a polyamine, hydroxyamine or polyol. Such materials are described, inter alia, in GB 1059847 and U.S. Pat. No. 3,269,946. The modified materials may be further modified by reaction with a reagent which is reactive with a functional group on the modified polyalk(en)yl succinic anhydride, such a reagent being, for example a dialkyl phosphonate, an oil-soluble organic acid such as tridecyl acid phosphate or an alkylbenzene sulphonic acid, a phosphorus acid-producing compound, a propane or butane sultone or an acid compound such as phosphoric acid, sulphuric acid or monochloroacetic acid. Such further modified materials are described, inter alia, in GB 1054093; GB 1054276; GB 1513178; GB 2083048; GB 2123429; FR 1464331; U.S. Pat. No. 3,502,677; EP 0017690 and EP 0156572.

Surfactants of the foregoing and other types can be used in a wide range of application but in general a particular surfactant is more suitable for use in some applications than in others. Surfactants can be used to form oil-in-water or water-in-oil emulsions and also dispersions of solids in a liquid phase, for example a coal in water slurry. However, some materials can be difficult to emulsify, for example modified alkyd resins and silicone resins. Hence, improved surfactant materials are desirable which can more readily emulsify materials, the formation of stable emulsions of which has, hitherto, been difficult.

U.S. Pat. No. 4,410,687 discloses polyesters obtained from a dicarboxylic acid or anhydride, an alkylene oxide derivative, a polyhydric compound and a fatty acid and the use of such polyesters as a dispersant resin in a coating composition. Generally similar materials are described in U.S. Pat. No. 3,457,206 but the emphasis in this disclosure is that the particular product described is a film-forming resin. Polyether ester polyols obtained by the sequential reaction of a polyoxyalkylene ether polyol, a dicarboxylic acid or derivative thereof and a diol are disclosed in U.S. Pat. No. 4,605,729. Further optional reagents may be used to prepare the products of U.S. Pat. No. 4,605,729 but no indication is given of the purpose of some of these optional reagents and there are no working examples disclosing the use of all the optional components.

According to the present invention there is provided a composition which is a reaction product of
(1) at least one compound containing at least one poly(oxyalkylene) group and having at least two —OH groups;
(2) at least one compound other than as defined in (1) which contains at least two reactive hydrogen atoms which are present as —OH, —NH$_2$ or —NHR groups;
(3) at least one carboxylic acid containing at least two carboxylic acid groups or the anhydride or chloride thereof; and
(4) at least one mono-carboxylic acid or at least one mono-hydroxy compound or at least one secondary mono-amino compound or at least one primary hindered mono-amine; where components (2) and (3) may be at least partially replaced by a compound containing both a reactive hydrogen atom and a carboxylic acid group; and R is a hydrocarbyl group or is an amino— or —OH substituted hydrocarbyl group.

A wide range of materials may be used as component (1) of the reaction mixture used to produce the composition of the present invention and for convenience hereafter these will be referred to as "poly(oxyalkylene) compounds". All of the poly(oxyalkylene) compounds which can be used as component (1) contain at least one poly(oxyalkylene) group which is typically of the type (AO)$_n$ where A is an alkylene group containing at least two carbon atoms and not more than six carbon atoms and the value of n is an integer with a value of at least two and typically is at least ten. The group A is, in general, an ethylene, propylene or butylene group particularly an ethylene group.

The poly(oxyalkylene) compounds may be condensates of a poly(oxyalkylene) group with a polyol, the relative proportions of poly(oxyalkylene) group to the polyol and the nature of polyol being such that compound contains at least two —OH groups, an example of such a compound being polyoxyethylene sorbitol containing one polyoxyethylene group in which the value of n is typically from 20 to 50. The polyol may be one containing only two —OH groups, in which case the polyoxyethylene chain is terminated by an —OH group but in general the polyol is one containing at least two —OH groups and the condensate contains only one poly(oxyethylene) chain.

Alternatively the poly(oxyalkylene) compound may be a block copolymer of two different poly(oxyalkylene) groups for example a poly(oxyethylene)-poly(oxypropylene)-poly(oxyethylene) polymer having two —OH groups, typically one in which at least 50% of the oxyalkylene units are oxyethylene units.

A further alternative poly(oxyalkylene) compound is a condensate with a diamine such as ethylenediamine or hexamethylene diamine. Typically in such a compound two poly(oxyalkylene) chains are attached to each nitrogen atom and the compound contains a total of four poly(oxyalkylene) chains, which may be the same as, or different from each other, and may be a block copolymer chain, for example a poly(oxypropylene)-poly(ox-7ethylene) sequence in which the poly(oxypropylene) is attached to the nitrogen atom of the diamine.

Yet a further type of poly(oxyalkylene) compound is one in which a poly(oxyalkylene) chain is attached as a side chain to a silicone such as a poly(dimethylsiloxane).

The molecular weight of the poly(oxyalkylene) compound is the weight average molecular weight and is typically in excess of 1000 for example at least 2500 and preferably is in excess of 5000 or even in excess of 10000.

More than one of the poly(oxyalkylene) compounds can be present in the composition of the present invention. Useful results have been obtained when the poly(oxyalkylene) compound is, or includes, a condensate with a diamine which condensate contains four poly(oxyalkylene) groups. The poly(oxyalkylene) compound may be a mixture of a diamine-poly(oxyalkylene) condensate with a polyol-poly(oxyalkylene) condensate and/or with a poly(dimethylsiloxane)-poly(oxyalkylene) condensate, preferably such mixtures in which the diamine-poly(oxyalkylene) condensate is at least 50%, especially at least 75% and more particularly at least 90% by weight.

Materials which may be used as component (2) of the reaction mixture used to produce the composition of the present invention will hereafter be referred to as "polyreactive compounds". The polyreactive compound may be a compound containing only two reactive hydrogen atoms, for example a diol such as ethylene glycol but it is preferred that at least a part, and especially all, of the polyreactive compound is a compound containing at least three reactive hydrogen atoms. The polyreactive compound may be an aliphatic, cycloaliphatic or aromatic compound. Thus, the polyreactive compound is conveniently a compound in which the reactive hydrogen atoms are present as —OH groups and examples of such polyreactive compounds include glycerol, pentaerythritol, sorbitol, pyrogallol or 1,3,5-trihydroxybenzene. Useful results have been obtained when the polyreactive compound is glycerol, pentaerythritol, sorbitol or a mixture of pentaerythritol and sorbitol.

The reactive hydrogen atoms in the polyreactive compound may be present as —OH groups, or as one or more —NH$_2$ groups or as —NHR groups. Alternatively a mixture of groups may be present. If the polyreactive compound contains a —NHR group, the group R is preferably an alkyl group and is typically a lower alkyl group which contains not more than six carbon atoms, and the group R may be substituted with a further amino group or groups and/or with one or more —OH groups. If the polyreactive compound contains amino groups, it may be a primary mono amine or may be an amine containing at least two amino groups, such a compound being referred to hereafter as a "polyamine".

The polyamine may be a diamine containing two —NH$_2$ groups or two —NHR$^1$ groups or with one —NH$_2$ group and one —NHR$^1$ group, where R$^1$ is an unsubstituted hydrocarbyl group. Examples of the polyamine include ethylene diamine; 1,2-diaminopropane; 1,3-diaminopropane; 1,4-diaminobutane and the higher homologues thereof; N-methylethylene diamine; N,N-dimethylethylene diamine; diethylenetriamine; tetraethylenepentamine and the like. The polyreactive compound may contain at least one —OH group and at least one amino group, which may be either —NH$_2$or —NHR$^1$, for example as in ethanolamine.

Component (2) is conveniently a compound in which all the reactive hydrogen atoms are present as —OH groups.

Materials which may be used as component (3) of the reaction mixture used to produce the composition of the present invention will hereafter be referred to as "polyacids". The polyacid may contain only two carboxylic acid groups and we have obtained useful products when using a polyacid which contains only two carboxylic acid groups or is the anhydride of such an acid compound. The polyacid may be a saturated or unsaturated aliphatic or cycloaliphatic compound or may be an aromatic compound. Thus, the polyacid may be malonic acid, succinic acid, glutaric acid, adipic acid, subaric acid, maleic acid, phthalic acid, terephthalic acid, isophthalic acid, trimellitic acid, pyromellitic acid, succinic anhydride, maleic anhydride, phthalic anhydride, pyromellitic dianhydride, terephthalic acid dichloride or adipic acid dichloride. Useful results have been obtained when the polyacid is phthalic anhydride.

Rather than using a polyreactive compound and a polyacid, the composition may be the reaction product obtained by replacing at least a part of the polyreactive compound and/or polyacid by a compound containing both a reactive hydrogen atom and a carboxylic acid group as in a hydroxycarboxylic acid or an aminocarboxylic acid (hereafter referred to as a "substituted carboxylic acid"). The substituted carboxylic acid may contain one —OH group or one amino group and one carboxylic acid group as in glycolic acid, lactic acid, salicylic acid, glycine, beta-aminopropionic acid and anthranilic acid. However, the use of a substituted carboxylic which contains either at least two reactive hydrogen atoms or two carboxylic acid groups may be preferred. Amino- and hydroxy-carboxylic acids may undergo self-condensation to form, for example, a lactide, a lactone, a polyamide or a polyester and such reactions are undesirable in the formation of the composition of the present invention. Hence, it is generally preferred that only a part of the polyreactive compound and/or polyacid is replaced by a substituted carboxylic acid.

Component (4) of the reaction mixture used to produce the composition of the present invention will hereafter be referred to as a "monoreactive compound". The monoreactive compound is preferably one containing at least four, and typically at least six, carbon atoms. The monoreactive compound may be a mono-acid and suitable mono-acids include hexanoic acid, octanoic acid and especially decanoic acid, tetradecanoic acid, octadecanoic acid, oleic acid and linoleic acid. Useful results have been obtained when the mono-acid is linoleic acid. Alternatively the monoreactive compound may be a mono-hydroxy compound such as hexanol, octanol, decanol, tetradecanol, octadecanol or the alkoxylated derivatives of any mono-hydroxy compound including methanol. The monoreactive compound may be a secondary mono-amino compound such as di-n-propylamine; di-n-hexylamine or N-methyl-N-n-hexylamine. Alternatively, component (4) of the reaction mixture may be a primary hindered mono-amine, that is an amine of the type $R^2NH_2$ in which the group $R^2$ contains at least 10, and preferably at least 15, carbon atoms. Component (4) may be a mixture of compounds but the monoreactive compounds should not be capable of reacting with each other and, in particular, the use of a mixture containing at least one mono-carboxylic acid together with at least one mono-hydroxy compound and/or at least one secondary mono-amino compound and/or at least one primary hindered mono-amine is very desirably to be avoided.

Preferably the composition of the present invention is essentially free of reactive hydrogen atoms such as —OH, —NH$_2$ and —NHR groups and also carboxylic acid groups. Typically the composition has an acid number of less than 12, preferably less than 10, especially less than 5 and particularly the acid number is not more than 2. The —OH number is also typically less than 5 and particularly not more than 3. The acid number and the —OH number can be determined in accordance with DGF: Einheitsmethode C-V 2 (1981) and DGF: Einheitsmethode C-V 17a (1953) respectively. If the composition is a polyester, typically it has a saponification number of 15 to 60, especially 25 to 50. The saponification number can be determined in accordance with DGF: Einheitsmethode C-V 3 (1977).

A preferred composition in accordance with the present invention has an —OH number of less than 5 and component (1) has a molecular weight in excess of 5000.

The materials used to obtain the composition of the present invention are preferably used in amounts to give a product which is essentially free of both reactive hydrogen atoms and carboxylic acid groups. Thus, the materials are used in amounts such that the reactive hydrogen atoms and the carboxylic acid groups are in essentially equimolar proportions, for example the molar ratio of reactive hydrogen atoms to carboxylic acid groups is in the range 0.75:1 up to 1.33:1 especially 0.90:1 to 1.1:1 and particularly 0.95:1 to 1.05:1.

The proportion of each particular component will be dependent on the molecular weight of the component, the number of —OH, —NH$_2$, —NHR or carboxylic acid groups it contains and also on the molecular weight of the product which is desired. It will be appreciated that the molecular weight of the product is dependent primarily on the proportion of component (4) which is used but is also dependent on the molecular weight of component (1).

Typically the proportion of the compound (or compounds) which is component (1) is from 10 to 95% by weight of the total reaction mixture and is typically at least 20% by weight of the total reaction mixture. If component (1) is a compound containing a poly(oxyalkylene) group of the type $(AO)_n$ in which n has a high value, for example at least 20 (hereafter such a material will be referred to as a "high molecular weight compound"), the proportion of component (.1) is then typically from 70 to 95% by weight, and particularly from 75 to 92% by weight, of the total reaction mixture. The proportion of the polyreactive compound (or compounds) which is component (2) is typically from 0.01 up to 40% by weight. if component (1) is a high molecular weight compound (as defined), then the proportion of component (2) is typically from 0.4 up to 5% by weight. The proportion of the polyacid (or polyacids) which is component (3) is typically from 1% up to 40% by weight. If component (1) is a high molecular weight compound (as defined), then the proportion of component (3) is typically from 1 up to 5% by weight. The proportion of the compound (or compounds) which is component (4) is typically from 4% up to 50% by weight. If component (1) is a high molecular weight compound (as defined) then the proportion of component (4) is typically from 4% up to 25% by weight, particularly from 6% up to 20% by weight. If a substituted carboxylic acid is used, this can replace some or all of the polyreactive compound and/or polyacid but preferably does not replace all of the polyreactive compound and/or polyacid.

The compounds used as components (1), (2), (3) and (4) may contain functional groups in addition to those specified but such additional functional groups should not react with the reactive hydrogen atoms or the carboxylic acid groups and preferably should not adversely affect the reactivity of the reactive hydrogen atoms or the carboxylic acid groups. Additional functional groups which may be present include halogen atoms, nitro and nitrile groups. In general we prefer that components (1), (2), (3) and (4) do not contain any additional functional groups and that the compound is a hydrocarbon compound, or oxyalkylene compound, which contains only the specified groups and which may, additionally, include a silicone.

A useful composition in accordance with the present invention is the reaction product of (1) an ethylene diamine alkoxylate having a molecular weight of at least 10000 and containing oxyethylene and oxypropylene groups where the oxyethylene groups are at least 60% by weight of the oxyalkylene groups;

(2) pentaerythritol or glycerol;

(3) phthalic acid and/or phthalic anhydride; and (4) linoleic acid.

Compositions of the foregoing type may additionally contain, as additional components (1), a poly(oxyethylene)-sorbitol condensate and/or a poly(dimethylsiloxane) having poly(oxyethylene) and/or poly(oxypropylene) side chains. The composition may further contain sorbitol as an additional component (2). Alternatively, but less preferred, component (1) is an ethylene oxide/propylene oxide/ethylene oxide block copolymer having two —OH groups. A further alternative composition, which is less preferred, is one in which component (4) is an amine such as soya amine.

The compositions of the present invention contain ester groups when the compositions are obtained by the reaction between compounds wherein the reactive hydrogen atoms are present as —OH groups and the carboxylic acid groups or anhydride or chloride groups. This reaction is an esterification reaction and can be effected under conventional esterification conditions.

Thus, compositions in accordance with the present invention, including some preferred compositions, can conveniently be obtained by the reaction of components (1), (2), (3) and (4) under esterification conditions. Conveniently all of the components are mixed together and reacted in a single step but, if desired, reaction can be effected in more than one step by adding at least one of the reactants to the mixture at a later stage, after at least some reaction has occurred. Typically, esterification is effected in the absence of any inert liquid solvent/diluent at an elevated temperature in the presence of an esterification catalyst.

The esterification is preferably effected at an elevated temperature which is at least 150° C. and preferably is at least 200° C. The esterification temperature preferably does not exceed 300° C.

Any suitable esterification catalyst may be used, for example phosphorus acid ($H_3PO_3$), p-toluenesulphonic acid, sodium methoxide, sodium hydroxide, potassium hydroxide or calcium hydroxide. A convenient esterification catalyst is phosphorous acid.

The esterification is conveniently effected at the elevated temperature for a time of at least 0.5 hours. In general, a reaction time of less than 10 hours is sufficient, especially not more than 6 hours. However, it will be appreciated that the reaction time is dependent on many factors including the rate of heating to the reaction temperature and the degree of agitation used, a fast rate of heating and vigorous agitation permitting a shorter time.

If the polyreactive compound is an amino compound, the reaction conditions will be those appropriate for the production of amide compounds and are generally very similar to, or even the same as, the reaction conditions used for the esterification.

The reaction product, which is a composition in accordance with the present invention, is discharged from the reaction vessel at an elevated temperature, whilst still in the liquid form and subsequently may be processed using conventional techniques to obtain the composition in any desired form.

The compositions of the present invention are typically solids which are dispersible in water and many are soluble in water to give 10% by weight solutions in water. The compositions are polymeric and are surfactants which are suitable for use in a wide range of applications in which conventional surfactants may be used.

Preferred compositions in accordance with the present invention have a critical micelle concentration at a concentration, in water, of $10^{-1}$ to 10% by weight. The preferred compositions give aqueous solutions having a surface tension which may be as low as $41 \pm 2$ mN/m.

Preferred compositions in accordance wi,,h the present invention give solutions of increased viscosity. Thus, a 10% by weight aqueous solution of a composition in accordance with the present invention preferably has a viscosity, measured at 25° C., which is greater than 1000 mpas and especially is at least 1500 mpas, the viscosity being measured using a Brookfield LVT viscometer using appropriate measuring conditions of spindle type and speed of rotation.

The compositions of the present invention may be used for the production of emulsions. If the emulsion is an oil-in-water emulsion, the oil phase in such an emulsion may be a resin such as an alkyd resin, a polyester resin or an epoxide resin. We have found that in many cases the minimum emulsifier concentration can be reduced and the emulsion obtained have an acceptable shelf life when using the compositions of the present invention. Thus, in oil-in-water emulsions using the compositions of the present invention as an emulsifier, the proportion of the emulsifier is typically in the range from 2 to 10% by weight of the emulsion, especially 3 to 6% by weight of the emulsion. If the resin is a silicone resin type, this type of resin is difficult to emulsify and, indeed, emulsification of such resins is not possible with many conventional emulsifiers. However, emulsification is possible with compositions in accordance with the present invention.

The compositions of the present invention may also be used to produce emulsions of silicone oils, for example silicone oils of viscosity 100 to 1000 cst, particularly 250 to 500 cSt. Similar proportions of emulsifier are used to produce emulsions of silicone oils as are used to produce resin emulsions.

The compositions of the present invention may also be used to produce emulsions of mineral oils, both crude and refined materials and waxes. The proportion of emulsifier is typically 2 to 10% by weight, especially 3 to 6% by weight in such emulsions.

Using the compositions of the present invention, an emulsion is conveniently prepared by mixing together the oil phase and the emulsifier and heating to a temperature which is typically at least 50° C. The oil phase containing the emulsifier is added to water, also at the elevated temperature, whilst mixing thoroughly. The mixture is homogenised to produce the desired emulsion, this typically requiring at least one minute, the time required to achieve a satisfactory emulsion depending on the size of the batch to be emulsified and the intensity of homogenisation. The emulsion is finally allowed to cool to ambient temperature whilst continuing to mix. The mixing and homogenisation can be effected using any means known for the formation of an emulsion. Thus, mixing and homogenisation can be effected using an Ultra Turrax or Silverson mixer, initial mixing being effected at a relatively low rate of stirring, typically not more than 1000 r.p.m., for example about 500 r.p.m., and homogenisation being effected at a higher rate of stirring, typically up to 10000 r.p.m., for example about 5000 r.p.m.

The compositions of the present invention may also be used to produce water-in-oil emulsions. Furthermore, using the compositions of the present invention, it is possible to obtain water-in-oil-in-water type emulsions which have hitherto been difficult to produce.

The compositions of the present invention may also be used to produce solid in liquid dispersions, for example dispersions of finely particulate solids in water having a solids content of at least 50% by weight which can be up to 80% by weight, depending on the particular solid and the particle size thereof. Dispersions in accordance with this aspect of the present invention may be formed as pumpable fluids which contain 70% by weight of coal or 60% by weight of titanium dioxide, with not more than 1% by weight of the composition of the present invention. The dispersions may be produced by any suitable technique for forming a dispersion such as by vigorously agitating a finely ground solid with a liquid phase, particularly water, which contains the composition of the present invention as a dispersing agent. Alternatively, mixing can be effected under conditions of high shear such as are experienced in a mill, for example a bead mill or a sand mill.

The compositions of the present invention may also be used to emulsify or disperse agrochemicals such as herbicides, insecticides or growth-regulating materials. More specifically; the herbicide Atrazine (6-chloro-N-ethyl-N'-isopropyl-1,3,5-triazine-2,4-diamine) can be dispersed at a level of between 45 and 50% by weight in a liquid mixture consisting predominantly of water using a composition in accordance with the present invention to achieve a suspension stability (determined as described in more detail in Example 30) of about 98%.

The various aspects of the present invention are described hereafter in more detail in the following non-limiting, illustrative examples in which proportions are by weight unless stated to the contrary.

Examples 1 to 5

Into a stainless steel vessel having a capacity of 3 dm³ and fitted with a stirrer were placed the ingredients set out in Table 1, in a total amount of 1 kg, together with 1 dm³ of water. The vessel was sealed and heated, with stirring, to 250°–260° C. On attaining the temperature of 250°–260° C., phosphorous acid ($H_3PO_3$) was introduced in an amount of 0.8% relative to the total weight of the ingredients.

The temperature was maintained at 250°–260° C., with stirring for a period of three hours and heating was then terminated. During the reaction, the mixture was monitored for —OH value and acid value by removing 5g samples of the mixture at intervals of half an hour. After the heating was terminated, the mixture was allowed to cool, with stirring, to about 150° C. The reaction product was obtained as a yellow/brown solid and was ground to particles of average size one mm.

The ingredients and proportions thereof used, together with the —OH value, acid value and saponification number are set out in Table 1.

TABLE 1

| Ex. | Ingredient (a) | % (b) | —OH (c) | Acid Value (d) | SAP No (e) |
|---|---|---|---|---|---|
| 1 | EDAA - 1 | 83.1 | <3 | <2 | 40 |
|   | POES - 1 | 3.8 |   |   |   |
|   | PT | 0.4 |   |   |   |
|   | ST | 0.9 |   |   |   |
|   | PA | 2.5 |   |   |   |
|   | LA | 9.3 |   |   |   |
| 2 | EDAA - 1 | 81.9 | <3 | <2 | ND |
|   | POES - 2 | 5.2 |   |   |   |
|   | PT | 0.4 |   |   |   |
|   | ST | 0.9 |   |   |   |
|   | PA | 2.4 |   |   |   |
|   | LA | 9.2 |   |   |   |
| 3 | EDAA - 2 | 70.2 | <3 | <2 | ND |
|   | POES - 1 | 6.7 |   |   |   |
|   | PT | 0.8 |   |   |   |
|   | ST | 1.5 |   |   |   |
|   | PA | 4.4 |   |   |   |
|   | LA | 16.4 |   |   |   |
| 4 | EDAA - 1 | 82.3 | <3 | <2 | ND |
|   | POES - 1 | 3.8 |   |   |   |
|   | PT | 0.5 |   |   |   |
|   | ST | 0.8 |   |   |   |
|   | PA | 3.4 |   |   |   |
|   | LA | 9.2 |   |   |   |
| 5 | EDAA - 1 | 84.3 | <3 | <2 | ND |
|   | POES - 1 | 3.9 |   |   |   |
|   | SIC | 2.5 |   |   |   |
|   | PT | 0.5 |   |   |   |
|   | PA | 1.7 |   |   |   |

TABLE 1-continued

| Ex. | Ingredient (a) | % (b) | —OH (c) | Acid Value (d) | SAP No (e) |
|---|---|---|---|---|---|
|   | LA | 7.1 |   |   |   |

Notes to TABLE 1
(a) EDAA - 1 is an alkoxylated ethylene diamine having a weight average molecular weight of 26000 with 80% of the oxyalkylene groups being oxyethylene groups, the remainder being oxypropylene groups.
EDAA - 2 is an alkoxylated ethylene diamine having a weight average molecular weight of 12500 with 70% of the oxyalkylene groups being oxyethylene groups, the remainder being oxypropylene groups.
POES - 1 is an ethoxylated sorbitol containing a single polyoxyethylene chain which contains, on average, 40 oxyethylene units.
POES - 2 is an ethoxylated sorbitol containing a single polyoxyethylene chain which contains, on average, 30 oxyethylene units.
SIC is a trimethylsilyl end-capped poly(dimethylsiloxane) containing, on average, 16 dimethylsiloxane units and having 3 or 4 polyoxyethylene side chains and available from Dow Corning as DC 193.
PT is pentaerythritol.
ST is sorbitol.
PA is phthalic anhydride.
LA is linoleic acid.
(b) % is weight % relative to the total weight of the ingredients.
(c) —OH is the —OH number determined in accordance with DGF: Einheitsmethode C-V 17a (1953) making allowance for the acid value determined as set out in Note (d).
(d) Acid value is determined in accordance with DGF: Einheitsmethode C-V 2 (1981).
(e) SAP No is the saponification number and is determined in accordance with DGF: Einheitsmethode C-V 3 (1977) making allowance for the acid value determined as set out in Note (d).
ND means this value was not determined.

Examples 6 to 27

A series of aqueous emulsions were prepared using the products of Examples 1 to 5 and, for comparative purposes, a number of commercially available surfactants.

The emulsions were all prepared using the following general procedure:

The oil phase material, together with the surfactant, were heated, with stirring, to 75° C. Water was separately heated to 75° C. The mixture of oil phase and surfactant, at 75° C., was added to water at 75° C. in an Ultra Turrax mixer operating at 500 r.p.m. On completing the addition of the oil phase mixture, the rate of agitation was increased to 5000 r.p.m. and was maintained for five minutes at 75° C. The rate of agitation was decreased to 500 r.p.m., the emulsion was allowed to cool to ambient temperature (20° to 25° C.) and was then removed from the Ultra Turrax mixer.

The components of the emulsions, the proportions thereof and the characteristics of the emulsions obtained are set out in Table 2.

TABLE 2

| Ex. | Component (f) | % (h) | Stability (i) |
|---|---|---|---|
| 6 | R - 1 | 60 | >14 days |
|   | 1 | 6 |   |
|   | Water | 34 |   |
| 7 | R - 1 | 60 | >14 days |
|   | 2 | 6 |   |
|   | Water | 34 |   |
| 8 | R - 1 | 60 | >14 days |
|   | 3 | 6 |   |
|   | Water | 34 |   |
| 9 | R - 1 | 60 | >14 days |
|   | 4 | 6 |   |
|   | Water | 34 |   |
| 10 | R - 1 | 60 | >14 days |
|   | 5 | 6 |   |
|   | Water | 34 |   |
| 11 | R - 1 | 60 | >14 days |
|   | 1 | 3 |   |
|   | Water | 37 |   |
| 12 | R - 3 | 60 | >14 days |
|   | 1 | 3 |   |

TABLE 2-continued

| Ex. | Component (f) | % (h) | Stability (i) |
|---|---|---|---|
| A | Water | 37 | <8 hours |
|  | R - 3 | 60 |  |
|  | EDAA - 1 | 6 |  |
| B | Water | 34 | <5 minutes |
|  | R - 3 | 60 |  |
|  | EDAA - 1 | 3 |  |
| 13 | Water | 37 | >14 days |
|  | R - 2 | 60 |  |
|  | 1 | 6 |  |
| 14 | Water | 34 | >14 days |
|  | R - 3 | 60 |  |
|  | 1 | 6 |  |
| 15 | Water | 34 | >14 days |
|  | R - 4 | 60 |  |
|  | 1 | 6 |  |
| 16 | Water | 34 | >14 days |
|  | R - 4 | 60 |  |
|  | 2 | 6 |  |
| 17 | Water | 34 | >14 days |
|  | R - 4 | 60 |  |
|  | 3 | 6 |  |
| 18 | Water | 34 | >14 days |
|  | R - 4 | 60 |  |
|  | 4 | 6 |  |
| 19 | Water | 34 | >14 days |
|  | R - 4 | 60 |  |
|  | 5 | 6 |  |
| 20 | Water | 34 | >14 days |
|  | R - 5 | 60 |  |
|  | 1 | 6 |  |
| 21 | Water | 34 | >14 days |
|  | SF | 25 |  |
|  | 1 | 5 |  |
| 22 | Water | 70 | >14 days |
|  | SF | 45 |  |
|  | 1 | 5 |  |
| 23 | Water | 50 | >3 <7 days |
|  | MO | 25 |  |
|  | 1 | 5 |  |
| 24 | Water | 70 | >3 <7 days |
|  | MO | 25 |  |
|  | 2 | 5 |  |
| 25 | Water | 70 | >14 days |
|  | MO | 25 |  |
|  | 3 | 5 |  |
| 26 | Water | 70 | >3 <7 days |
|  | MO | 25 |  |
|  | 4 | 5 |  |
| 27 | Water | 70 | >3 <7 days |
|  | MO | 25 |  |
|  | 5 | 5 |  |
|  | Water | 70 |  |

Notes to TABLE 2
(a) is as defined in Notes to Table 1.
(f) R - 1 is an alkyd resin of short oil length and is available from Texaco as Rhenalyd R 320.
R - 2 is a 50/50 blend of Rhenalyd R 320 and Rhenalyd M 750.
R - 3 is an alkyd resin of long oil length and is available from Texaco as Rhenalyd M 750.
R - 4 is a polyester resin which is available from Bayer as Roskydal 502.
R - 5 is an epoxide resin which is available from Shell Chemicals as Epikote 818.
SF is a silicone fluid of viscosity 350 cSt which is available from Imperial Chemical Industries PLC as silicone fluid F 111/350.
MO is a mineral oil which is available from Exxon Chemicals as Coray 10.
(h) % is % weight of the total emulsion.
(i) The emulsion after preparation is stored in an oven at 40° C. and is assessed for separation and/or inhomogeneity shortly after being prepared (before being placed in the oven) and after periods of 8 hours, 1, 3, 7 and 14 days.

Example 28

A coal in water slurry was obtained using the following procedure.

The emulsifiers were added to water and the aqueous mixture was stirred using a multi-blade stirrer at a stirrer tip speed of 4.5 m/second. Stirring was continued and the coal was added slowly until the amount of coal added was 70% by weight of the slurry, and stirring was then continued for a further five minutes. The resulting slurry had the composition as set out in Table 3.

TABLE 3

| Component (j) | % weight |
|---|---|
| Coal | 70 |
| 1 | 0.5 |
| QTA | 0.25 |
| Water | 29.475 |

Notes to TABLE 3
(j) Coal is Prosper-Kohle 2 from the Prosper mine of the ROG Company of West Germany. The coal used had a particle size such that at least 80% by weight of the coal had a particle size of less than 100 micrometres.
1 is the product of Example 1.
QTA is diethyl sulphate quaternary hydrogenated tallow amine ethoxylated with about 20 moles of ethylene oxide for each mole of the amine.

The mixture obtained was a free flowing coal in water slurry having a viscosity of 1200 mPa.s$^{-1}$ as determined at 25° C. using a Brookfield LVT viscometer with a No. 3 spindle operating at 60 r.p.m.

When the foregoing procedure was repeated replacing the product of Example 1 by an equal proportion by weight of an alkoxylated hexamethylene diamine having a weight average molecular weight of about 22000 and with 80% of the oxyalkylene groups being oxyethylene groups, the remainder being oxypropylene groups, a free flowing slurry was not obtained and the slurry viscosity could not be determined.

Example 29

A dispersion of titanium dioxide in water was prepared using 60% by weight of titanium dioxide, 1% by weight of the product of Example 1, the remainder being water.

The materials were mixed using the procedure described for the coal in water slurry in Example 28 with the exception that stirring was terminated when the addition of titanium dioxide was completed. The mixture obtained was transferred into a bead mill (available from Dyno-Mill) containing glass beads of 1 mm diameter. Milling was effected for two minutes and the dispersion was removed from the mill.

The resulting mixture was a free flowing, stable dispersion of titanium dioxide in water which showed no settled solid after standing for four weeks at ambient temperature. The titanium dioxide had a particle size of less than one micrometer as determined using a Grindometer available from Erichson of West Germany.

Example 30

A pesticide flowable composition was prepared using the procedure described in Example 29. The composition contained 45.7% by weight of Atrazine (6-chloro-N-ethyl-N'-isopropyl-1,3,5-triazine-2,4-diamine), 4.5% by weight of glycerol, 4.5% by weight of propylene glycol, 4.5% by weight of the product of Example 1, the remainder being water.

The stability of the pesticide flowable composition was determined by placing a known volume of the composition into a measuring cylinder. The cylinder was inverted 30 times and allowed to stand for 30 minutes. The upper 90% of the liquid was withdrawn with a suction tube, taking care not to disturb any sediment. The remaining 10% of the liquid was transferred to an evaporating dish and dried to a constant weight in an oven at 50° C. The residual powder was weighed accurately. The % suspensibility was obtained from the relationship $$\% \text{ suspensibility} = \frac{10}{9} \times \frac{100(X - Y)}{X}$$

where

X is the weight of the components of the pesticide flowable composition with the exception of water; and Y is the weight of the residual powder.

Using the foregoing procedure the pesticide flowable composition was found to have a % suspensibility of about 98%.

Examples 31 to 33

The procedure used in Examples 1 to 5 was repeated using different ingredients and proportions of ingredients.

The ingredients and the proportions thereof used, together with the —OH value, acid value and saponification number are set out in Table 4.

TABLE 4

| Ex. | Ingredient (a) (k) | % (b) | —OH (c) | Acid Value (d) | SAP No (e) | M.Pt. (°C.) |
|---|---|---|---|---|---|---|
| 31 | EDAA - 1 | 86.85 | 0.4 | 10.4 | 30.5 | 55 |
|  | GL | 1.35 |  |  |  |  |
|  | PA | 2.50 |  |  |  |  |
|  | LA | 9.30 |  |  |  |  |
| 32 | EO/PO | 86.85 | 4.3 | 6.4 | 17.4 | 77 |
|  | GL | 1.35 |  |  |  |  |
|  | PA | 2.50 |  |  |  |  |
|  | LA | 9.30 |  |  |  |  |
| 33 | EDAA - 1 | 86.85 | 3.0 | 5.3 | 30.6 | 30 |
|  | GL | 1.35 |  |  |  |  |
|  | PA | 2.50 |  |  |  |  |
|  | SA | 9.30 |  |  |  |  |

Notes to TABLE 4
(a) to (e) are all as defined in Notes to Table 1.
(k) GL is glycerol
EO/PO is an ethylene oxide/propylene oxide/ethylene oxide block copolymer with two —OH end group and having an average molecular weight of 4650 and 50% by weight of polymerised ethylene oxide.
SA is soya amine which is predominantly a primary mono-amine in which the hydrocarbyl groups are a mixture of tetradecyl (1%), hexadecyl (25%), octadecyl (8%) and octadecenyl (66%) groups.

Examples 34 to 39

A series of aqueous emulsions were prepared using the products of Examples 31 to 33 using the procedure described for Examples 6 to 27.

The components of the emulsions, the proportions thereof and the characteristics of the emulsions obtained are set out in Table 5.

TABLE 5

| Ex. | Component (f) | % (h) | Stability (i) |
|---|---|---|---|
| 34 | R - 3 | 60 | >14 days |
|  | 31 | 6 |  |
|  | Water | 34 |  |
| 35 | R - 3 | 60 | >7 <14 days |
|  | 32 | 6 |  |
|  | Water | 34 |  |
| 36 | R - 3 | 60 | >7 <14 days |
|  | 33 | 6 |  |
|  | Water | 34 |  |
| 37 | SF | 25 | >7 <14 days |
|  | 31 | 5 |  |
|  | Water | 70 |  |
| 38 | SF | 25 | <1 day |
|  | 32 | 5 |  |
|  | Water | 70 |  |
| 39 | SF | 25 | <1 day |
|  | 33 | 5 |  |
|  | Water | 70 |  |

Examples 40 to 42

The procedure of Example 29 was repeated using the products of Examples 31 to 33.

Using the product of Example 31, the mixture obtained was a free flowing, stable dispersion which showed no settled solid after standing for four weeks at ambient temperature.

Using the product of Example 32, the mixture obtained was a free flowing, water thin dispersion which showed some slight sedimentation after standing for four weeks at ambient temperature.

Using the product of Example 33, the mixture obtained was a dispersion which, after standing for four weeks at ambient temperature, became a solid block which was not readily dispersed.

Examples 43 to 46

Aqueous solutions containing the products of Examples 1, 31, 32 and 33 were prepared containing different concentrations of the product. The surface tension of each solution was obtained by the du Nony method using a tensiometer K10 available from Messrs.Kruss. The surface tension of the aqueous solution at different concentrations of the products are set out in Table 6.

TABLE 6

| Concentration | Surface Tension (mN/m) | | | |
|---|---|---|---|---|
| (g/100 g H$_2$O) | 1 | 31 | 32 | 33 |
| $10^{-5}$ | 70.2 | 71.0 | 70.4 | 72.1 |
| $10^{-4}$ | 65.0 | 64.0 | 66.5 | 57.7 |
| $10^{-3}$ | 52.8 | 57.6 | 60.8 | 50.3 |
| $10^{-2}$ | 49.1 | 48.8 | 49.3 | 39.2 |
| $10^{-1}$ | 42.4 | 43.1 | 45.5 | 37.9 |
| 1 | 41.3 | 41.6 | 43.3 | 37.1 |
| 10 | 41.6 | 42.9 | 42.5 | 36.2 |

It will be observed that the products of Examples 1 and 31 show a minimum surface tension at a concentration of about 1% by weight and this indicates that the critical micelle concentration is also about 1% by weight for these materials.

Examples 47 to 50

10% by weight aqueous solutions of the products of Examples 1, 31, 32 and 33 were prepared. The viscosity of each solution was determined using a Brookfield LVT viscometer operating at 6 r.p.m. at 25° C.

The spindle used was varied and this is reported in Table 7 together with the viscosity of each solution.

TABLE 7

| Example | Compound | Spindle | Viscosity (mPa s) |
|---|---|---|---|
| 47 | 1 | C | 2000 |
| 48 | 31 | E | 11000 |
| 49 | 32 | A | 550 |
| 50 | 33 | A | 400 |

I claim:

1. A Composition which contains ester and/or amide groups and is the product of the reaction of components (1), (2), (3) and (4) wherein (1) is an alkylene diamine-poly(oxyalkylene) condensate and the poly(oxyalkylene) group is of the formula (AO)$_n$H where A is C$_{2-6}$ alkylene and n is at least 20;

(2) a polyreactive compound selected from the group consisting of glycerol; pentaerythritol; sorbitol; pyrogallol; 1,3,5-trihydroxybenzene; ethylenediamine; 1,2-diaminopropane; 1,3-diaminopropane; diaminobutane; N-methylethylenediamine; N,N-dimethylethylenediamine; diethylenetriamine; tetraethylenepentamine and ethanolamine;

(3) a carboxylic acid containing at least two carboxylic acid groups or the anhydride or chloride thereof; and (4) a monoreactive compound selected from the group consisting of a mono carboxylic acid, a monohydroxy compound, a secondary mono-amino compound and an amine of formula $R^2NH_2$ wherein $R^2$ contains at least 10 carbon atoms; and where Components (2) and (3) may be at least partially replaced by a compound containing both a reactive hydrogen atom and a carboxylic acid and wherein components (1), (2), (3) and (4) are reacted together in the proportions by weight of 70 to 95% of (1);
0.4 to 5% of (2);
1 to 5% of (3); and
4 to 25% of (4).

2. The composition of claim 1 wherein component (4) is a mono-carboxylic acid, a mono-hydroxy compound or a secondary mono-amino compound.

3. The composition of claim 1 which has an acid number of less than 12 and an —OH number of less than 5.

4. The composition of claim 1 which has an acid value of less than 5.

5. The composition of claim 1 which has an acid value of less than 3.

6. The composition of claim 1 wherein component (3) is a dicarboxylic acid, anhydride or chloride thereof.

7. The composition of claim 1 wherein component (1) has a molecular weight in excess of 10,000.

8. The composition of claim 1 wherein A is ethylene or propylene or mixtures thereof.

9. The composition of claim 1 which additionally contains a poly(oxyalkylene) polyol containing at least two —OH groups wherein the poly(oxyalkylene) group is of the formula $(AO)_nH$ where A is $C_{2-6}$ alkylene and n is at least 20 and the poly(oxyalkylene) polyol is present in an amount not exceeding that of component (1).

10. The composition of claim 9 wherein the polyol is sorbitol.

11. The composition of claim 1 wherein component (4) is a monocarboxylic acid selected from the group consisting of hexanoic acid, octanoic acid, decanoic acid, tetradecanoic acid, octadecanoic acid, oleic acid and linoleic acid.

12. The composition of claim 1 which is the product of the reaction of components (1), (2), (3) and (4) in the presence of phosphorous acid.

13. A composition which contains ester and/or amide groups and is the product of the reaction of components (1), (2), (3) and (4) wherein (1) is an alkylene diamine-poly(oxyalkylene) condensate and the poly(oxyalkylene) group is of the formula $(AO)_nH$ where A is $C_{2-6}$ alkylene and n is at least 20;

(2) a polyreactive compound selected from the group consisting of glycerol; pentaerythritol; sorbitol; pyrogallol; 1,3,5-trihydroxybenzene; ethylenediamine; 1,2-diaminopropane; 1,3-diaminopropane; diaminobutane; N-methylethylenediamine; N,N-dimethylethylenediamine; diethylenetriamine; tetraethylenepentamine and ethanolamine;

(3) a carboxylic acid selected from the group consisting of malonic, succinic, glutaric, adipic, subaric, maleic, phthalic, terephthalic, isophthalic, trimellitic and pyromellitic acids, succinic anhydride, maleic anhydride, phthalic anhydride, pyromellitic anhydride, terephthalic acid dichloride and adipic acid dichloride; and (4) a monoreactive compound selected from the group consisting of a mono carboxylic acid, a monohydroxy compound, a secondary mono-amino compound and an amine of formula $R^2NH_2$ wherein $R^2$ contains at least 10 carbon atoms; and where Components (2) and (3) may be at least partially replaced by a compound containing both a reactive hydrogen atom and a carboxylic acid and wherein components (1), (2), (3) and (4) are reacted together in the proportions by weight of 70 to 95% of (1);
0.4 to 5% of (2);
1 to 5% of (3); and
4 to 25% of (4).

14. A composition which is the reaction product of (1) an ethylenediamine alkoxylate having a molecular weight of at least 10,000 and containing oxyethylene and oxypropylene groups wherein the oxyethylene groups are at least 60% by weight of the oxyalkylene groups;

(2) is pentaerythritol;

(3) is phthalic anhydride;

(4) is linoleic acid; and (5) an ethoxylated sorbitol containing a single polyoxyethylene chain having at least 20 oxyethylene groups wherein components (1), (2), (3), (4) and (5) are reacted together in the proportions, by weight, of 70 to 95% of (1);
0.4 to 5% of (2);
1 to 5% of (3);
4 to 25% of (4); and
up to 10% of (5) relative to component (1).

15. A composition which contains ester and/or amide groups and is the reaction product of the following:

(1) an alkylene diamine-poly(oxyalkylene) condensate wherein the poly(oxyalkylene) group is of the formula $(AO)_nH$ where A is $C_{2-6}$ alkylene and n is at least 20;

(2) a polyreactive compound selected from the group consisting of glycerol; pentaerythritol; sorbitol; pyrogallol; 1,3,5-trihydroxybenzene; ethyelenediamine; 1,2-diaminopropane; 1,3-diaminopropane; diaminobutane; N-methylethylenediamine; N,N-dimethylethylenediamine; diethylenetriamine; tetraethylenepentamine and ethanolamine;

(3) a carboxylic acid containing at least two carboxylic acid groups or the anhydride or chloride thereof;

(4) a monoreactive compound selected from the group consisting of a mono carboxylic acid, a monohydroxy compound, a secondary mono-amino compound and an amine of formula $R^2NH_2$ wherein $R^2$ contains at least 10 carbon atoms; and where Components (2) and (3) may be at least partially replaced by a compound containing both a reactive hydrogen atom and a carboxylic acid and wherein components (1), (2), (3) and (4) are reacted together in the following proportions, by weight of components (1)-(4):
70 to 95% of (1);
0.4 to 5% of (2);
1 to 5% of (3);
4 to 25% of (4); and
a poly(oxyalkylene) silicone which is present in an amount not exceeding that of component (1).

16. The composition of claim 15 wherein silicone is trimethylsilyl end-capped poly(dimethylsiloxane).

* * * * *